(12) United States Patent
Oplatek et al.

(10) Patent No.: US 10,184,282 B2
(45) Date of Patent: Jan. 22, 2019

(54) DOOR CLOSING AND SECURING MECHANISM

(71) Applicant: BMT Medical Technology s.r.o., Brno (CZ)

(72) Inventors: Igor Oplatek, Brno (CZ); Lubor Trčka, Brno (CZ); Michal Foltýn, Brno (CZ)

(73) Assignee: BMT Medical Technology s.r.o., Brno (CZ)

( * ) Notice: Subject to any disclaimer, the term of this patent is extended or adjusted under 35 U.S.C. 154(b) by 799 days.

(21) Appl. No.: 14/632,836

(22) Filed: Feb. 26, 2015

(65) Prior Publication Data

US 2015/0240545 A1 Aug. 27, 2015

(30) Foreign Application Priority Data

Feb. 26, 2014 (CZ) .................................... 2014-116

(51) Int. Cl.
*E05F 1/10* (2006.01)

(52) U.S. Cl.
CPC .............. *E05F 1/10* (2013.01); *Y10T 16/585* (2015.01)

(58) Field of Classification Search
CPC ........... Y10T 292/089; Y10T 292/1062; Y10T 292/0948; Y10T 292/1053; Y10T 292/081; Y10T 292/0936; E05B 53/003; E05B 15/101; E05B 65/0852
USPC ......................................................... 292/95
See application file for complete search history.

(56) References Cited

U.S. PATENT DOCUMENTS

| 2,128,014 | A | * | 8/1938 | Platin | ..................... E05B 17/22 200/61.67 |
| 2,378,654 | A | | 6/1945 | Pekny | |
| 2,777,722 | A | * | 1/1957 | Burke | ................ E05B 65/0046 292/332 |
| 2,926,945 | A | * | 3/1960 | Clark | ..................... E05C 19/02 292/110 |

(Continued)

FOREIGN PATENT DOCUMENTS

| DE | 29812603 U | 9/1998 |
| DE | 29812603 U1 | 9/1998 |

OTHER PUBLICATIONS

European Search Report dated Jun. 14, 2016 for European Application No. EP 15000525 filed Feb. 24, 2015.

*Primary Examiner* — Mark A Williams
(74) *Attorney, Agent, or Firm* — Avery N. Goldstein; Blue Filament Law PLLC

(57) ABSTRACT

Door closing and securing mechanism, particularly a mechanism for closing and securing doors of laboratory, which mechanism consist of a fixed part (9) attached to the respective cabinet (12) and a movable part (14) arranged in the door (1), wherein the movable part comprises at least one plate (3) provided with flexible end stops (4) and inseparably coupled with the handle (2) by means of a center pin (10) with a coaxial end stop (7) attached thereto, the plate (3) being further provided with a pivot (5) eccentrically mounted thereon and carrying at least one pivotally arranged hook (8), which has a recess for engaging a protrusion of the fixed part (9), with an opening accommodating one end of a tensile spring (11) and with a second spring (6) formed by a compression spring arranged between the plate (3) and the hook (8).

2 Claims, 5 Drawing Sheets

(56) References Cited

U.S. PATENT DOCUMENTS

| | | | | |
|---|---|---|---|---|
| 3,189,375 A | * | 6/1965 | Getman | F16P 3/08 |
| | | | | 292/111 |
| 3,191,244 A | | 6/1965 | Burke | |
| 3,244,830 A | * | 4/1966 | Bates | A47L 15/4259 |
| | | | | 200/61.68 |
| 3,325,200 A | * | 6/1967 | Fowler | A47L 15/4259 |
| | | | | 292/111 |
| 3,367,697 A | * | 2/1968 | Fox, Sr. | F24C 15/022 |
| | | | | 292/113 |
| 3,647,251 A | | 3/1972 | Brown et al. | |
| 4,174,860 A | * | 11/1979 | Shea | F24C 15/022 |
| | | | | 292/113 |
| 6,079,754 A | | 6/2000 | Alexy | |
| 6,364,376 B1 | * | 4/2002 | Spargo | A47L 15/4259 |
| | | | | 292/97 |
| 8,403,380 B2 | | 3/2013 | Ballhause | |
| 8,844,514 B2 | | 9/2014 | Steurer | |
| 2002/0056296 A1 | * | 5/2002 | Weinerman | E05B 13/105 |
| | | | | 70/79 |
| 2012/0019112 A1 | | 1/2012 | Steurer | |

* cited by examiner

DOOR CLOSING AND SECURING MECHANISM

FIELD OF THE INVENTION

The present invention relates to a door closing and securing mechanism, particularly a mechanism for closing and securing doors of laboratory, medical and/or sterilization cabinets.

BACKGROUND OF THE INVENTION

The known door locking and securing mechanisms, which constitute the prior art and are typically used in the doors of medical devices, sterilizers or laboratory apparatuses, are usually conceived as linkage-type mechanisms.

A known door closing mechanism is operated by means of a handle that is rigidly coupled with hooks. The axis of rotation of the hooks is identical to that of the handle. The movement of the handle causes the hooks to be driven in rotation. Once the mutual engagement of the hooks and the fixed part of the closing mechanism, which is attached to a cabinet, is achieved, the continuing movement of the handle causes the door to start moving towards the cabinet. The movement of the door, however, is accompanied by the friction between the hooks and the fixed part of the closing mechanism. The frictional force is inversely proportional to the distance between the door and the cabinet at any given moment. The above effect hinders the door from being closed or opened in a convenient manner. Moreover, it is often accompanied with undesirable acoustic emissions.

The U.S. Pat. No. 8,403,380 B2 discloses a cover closure for housing cover of laboratory and the like, in particular for centrifuge housings, in which a cover hook is engaged by a closure hook and brought into a closing position. The closing and opening movement of the closure hook is essentially caused by an eccentric in connection with a crank guide and a guide path.

The U.S. Pat. No. 2,128,014 A discloses a door lock enabling the door to be opened and closed from the inside at any time, whereas to be opened from the outside only upon having last been closed from outside. According to one of its embodiment, the door lock comprises two lock handles concentrically mounted on each other in such manner that the outer handle (pointing outwards) is movable on the spindle of the inner handle (pointing inwards). The apparatus further comprises a lock bolt displaceably attached to a disc by means of two pins secured on the disc, projecting into a slit in the bolt. The disc is rotatably mounted on the spindle of the handle and the bolt is provided with a transverse recess to engage with a contact flap for locking. There is a helical spring inserted between the disc and the bolt forcing the bolt outwardly in the closing phase and another helical spring returning the inner handle into its initial opened position. The presence of two handles requires additional features to be included in the movement of the locking mechanism, namely a lever, a pawl and a plurality of pins. By rotating the outer handle, the movement of the bolt towards the contact flap is translational and delimited by two pins secured on the disc. The bolt 12 slides against the pins 40, 41 which are not located on the rotational axis of the outer handle 9. Furthermore, the transverse recess merely inserts itself in the contact flap, it is not secured by a hooking movement. By rotating the inner handle, the movement of the bolt towards the contact flap is circular, not along a curved trajectory, thereby hooking the transverse recess of the bolt in the contact flap. However, the hooking movement does not produce any backward movement of the transverse recess or pull of the door towards the door frame.

SUMMARY OF THE INVENTION

The present invention proposes a novel design solution for door closing and securing mechanisms. The design solution according to the invention is simple and enables the particular door to be easily closed and opened.

The above mentioned drawbacks are largely eliminated by a door closing and securing mechanism, particularly a mechanism for closing and securing doors of laboratory, medical and/or sterilization cabinets, wherein the mechanism consists of a fixed part attached to a cabinet, and a movable part arranged in a door. The movable part comprises at least one plate provided with a first and a second flexible end stop in order to delimit the movement of the plate. The plate is fixedly coupled with a handle by means of a center pin. The center pin forms a rotational axis of the handle, is pivotally interconnected with the door and has a coaxial end stop attached thereto. The plate is further provided with a pivot eccentrically mounted thereon, wherein the pivot forms a rotational axis for at least one pivotally arranged hook with a recess at its swinging end for engaging a protrusion of the fixed part. It is important to note that the rotational axis of the handle is not identical with the rotational axis of the hook.

A tensile spring is attached at its one end to the plate, preferably in the vicinity of the center pin, and at its other end to the door in order to secure the attachment of the plate to the door. A compression spring is attached at its one end to the hook, preferably in the vicinity of the recess of the hook, and at its other end to the plate in the vicinity of the second flexible end stop in order to secure the attachment of the hook to the fixed part.

According to the invention, the door closing and securing mechanism consists of a fixed part and a movable part, one or more of the components of the latter performing an eccentric movement in order to pull the door towards the respective cabinet. The movements of the handle and the hook are rotational and the swinging end of the hook moves along a curved trajectory.

The main advantage of the door provided by the closing and securing mechanism according to the invention consists in that the opening and closing operation of such door can be considerably facilitated. The door opening and closing operations are carried out through the corresponding movements of the handle requiring just a minimum force to be exerted, the movements of the internal eccentric mechanism being derived from those of the handle.

Furthermore, the technical solution, on which the door closing and securing mechanism according to the present invention is based, enables the force required both for closing the respective cabinet and for opening the same to be kept at a minimum level.

Another advantage of the invention consists in the simple design solution of the closing and securing mechanism.

BRIEF DESCRIPTION OF THE DRAWINGS

The invention will be further explained with reference to the accompanying drawings, in which.

EXAMPLES OF PREFERRED EMBODIMENTS OF THE INVENTION

Figure 1:
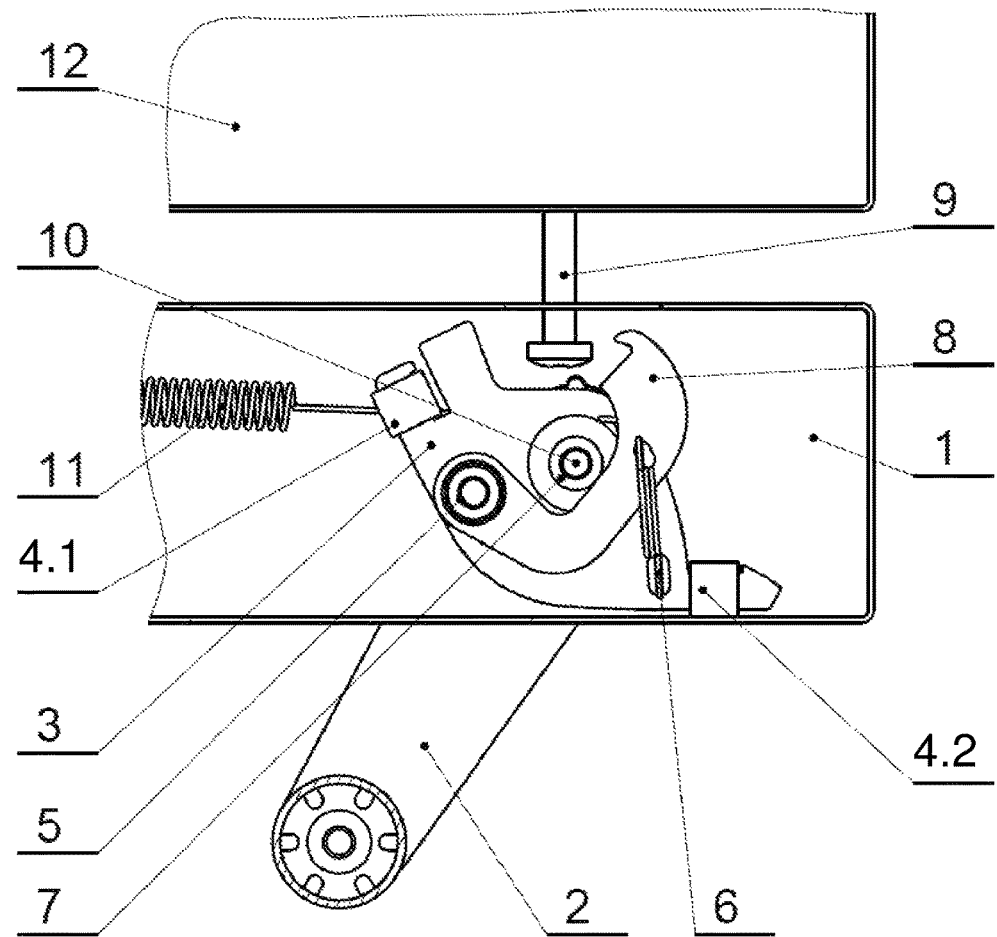
FIG. 1 shows the door closing and securing mechanism in its open position.

Hereinafter, an exemplary preferred embodiment of the present invention will be described with reference to the corresponding accompanying drawings.

The door closing and securing mechanism according to the present invention consists of the fixed part 9, which is arranged on the cabinet 12, and of the movable part 14, which is situated in the door 1 and comprises a plurality of interacting components (2, 3, 4.1, 4.2, 5, 6, 7, 8, 10, 11), the movement trajectories of the individual components (3, 4.1, 4.2, 5, 6, 7, 8, 10, 11) being derived from that of the handle 2. As clearly illustrated in FIGS. 1, 2, 3, and 4, the movable part 14 according to the present embodiment of the closing and securing mechanism comprises the plate 3 that is fixedly coupled with the handle 2 by means of the center pin 10. The center pin 10 forms a rotational axis of the handle 2, is pivotally interconnected with the door 1 and has a coaxial end stop 7 attached thereto. The end positions of the plate 3 are delimited by the first flexible end stop 4.1 and the second flexible end stop 4.2. Furthermore, the plate 3 is provided with the pivot 5 eccentrically mounted thereon and the pivot 5 forms a rotational axis for the movable hook 8 having a recess at its swinging end. The hook 8 and the plate 3 are interconnected by means of the compression spring 6 in order to force the hook 8 towards the fixed part 9 or towards the coaxial end stop 7. The compression spring 6 is attached at its one end to the hook 8 in the vicinity of the recess thereof and at its other end to the plate 3 in the vicinity of the second flexible end stop 4.2, in order to secure the attachment of the hook 8 to the fixed part 9. The coaxial end stop 7 is arranged coaxially with respect to the center pin 10 of the plate 3. The shape of the hook 8 having the recess enables the hook 8 to engage with the protrusion of the fixed part 9. Due to the eccentric arrangement of the pivot 5, the hook 8 approaches the fixed part 9 during the phase of the closing movement of the door 1 corresponding to the final phase of the movement of the handle 2 (see FIGS. 2 and 3). This causes the door 1 to be pulled towards the cabinet 12. During the phase of the opening movement of the door 1 corresponding to the final phase of the movement of the handle 2 (see FIG. 1), the hook 8 will rest against the end stop 7 which causes the hook 8 to move away from the fixed part 9 and enables the door 1 to be opened.

Figure 2:
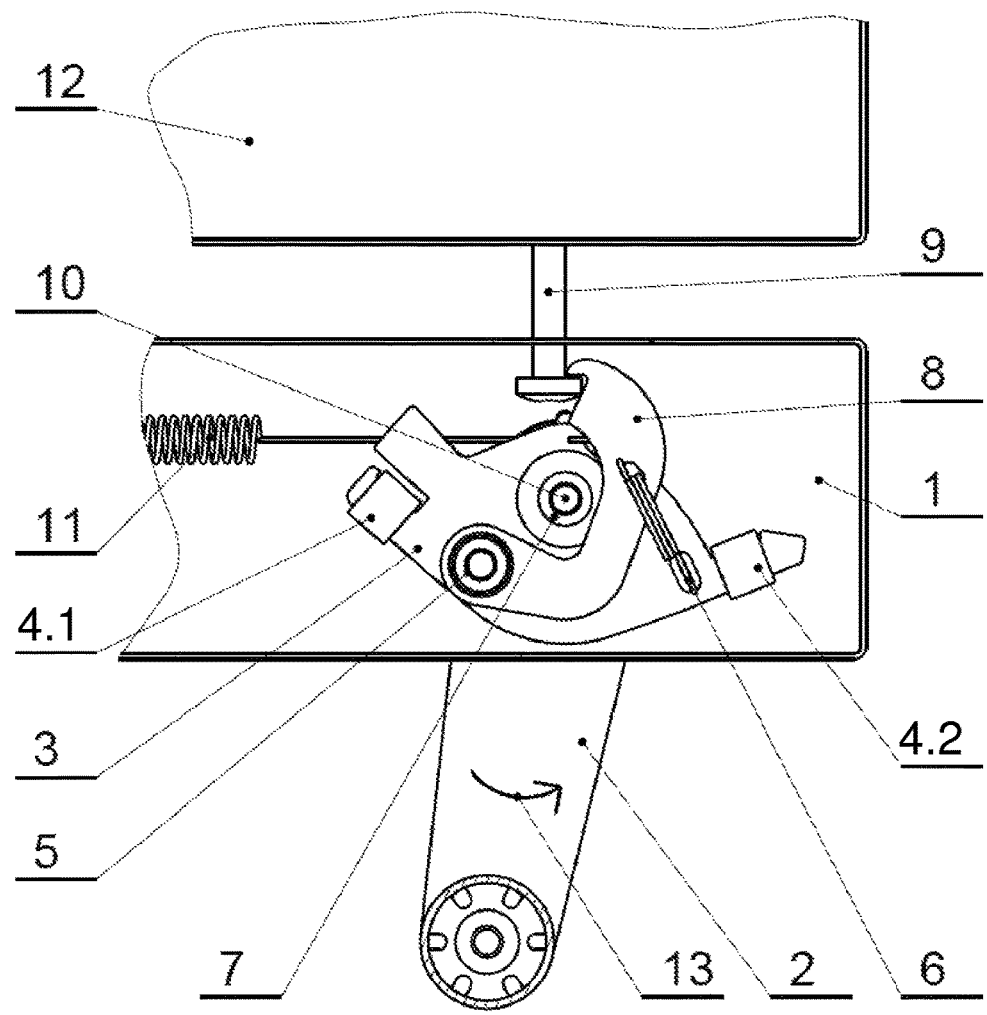
FIG. 2 shows the door closing and securing mechanism in the door closing a door-closing position.
Figure 3:
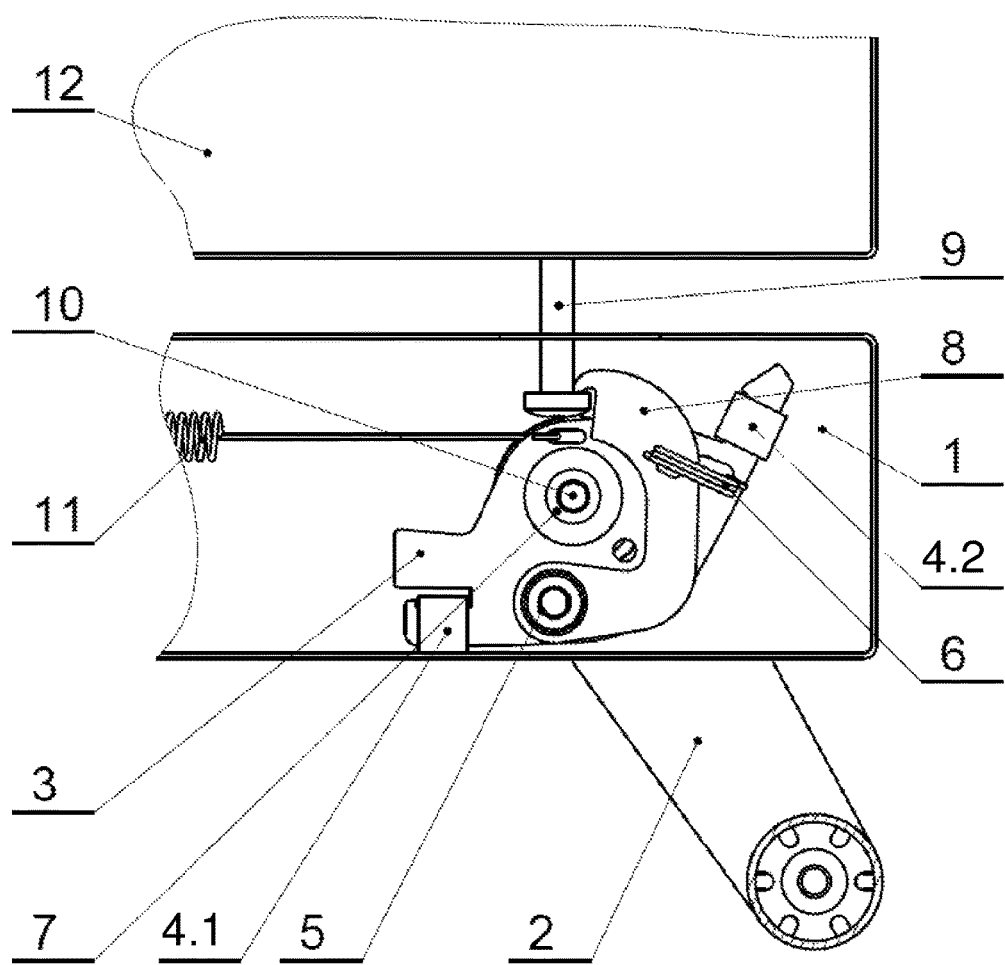
FIG. 3 shows the door closing and securing mechanism in its closed position.
Figure 4:
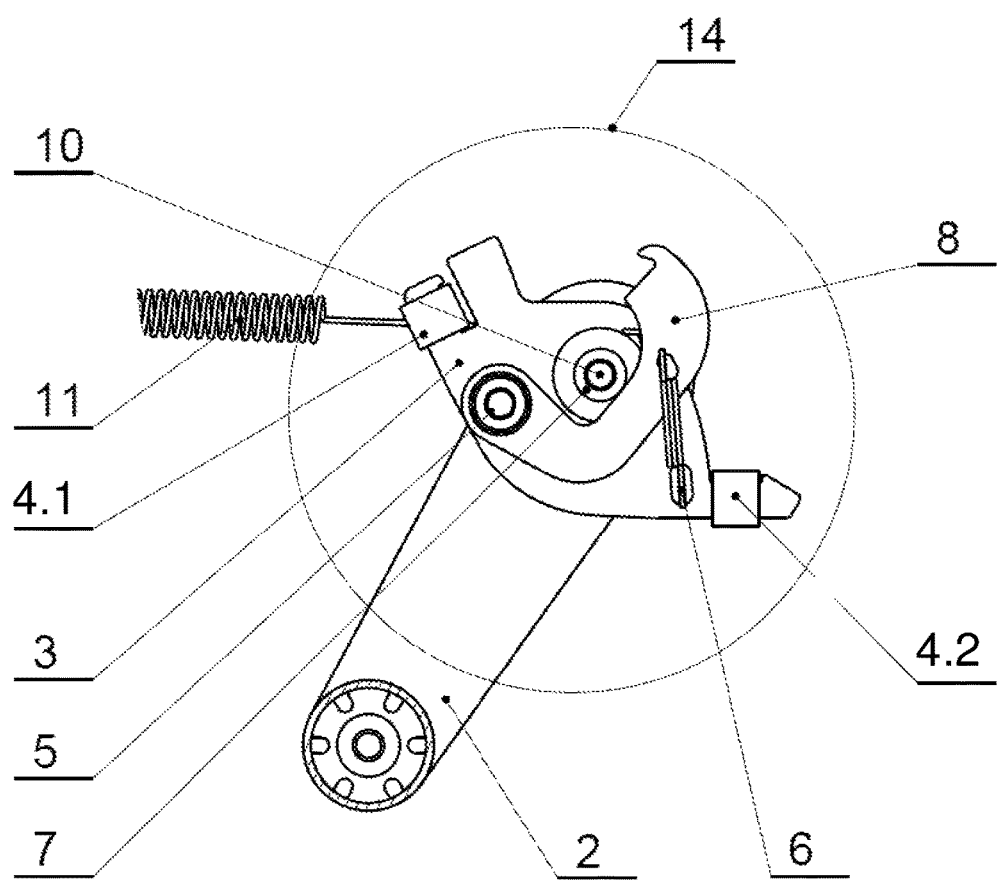
FIG. 4 shows the movable part of the door closing and securing mechanism.
Figure 5:
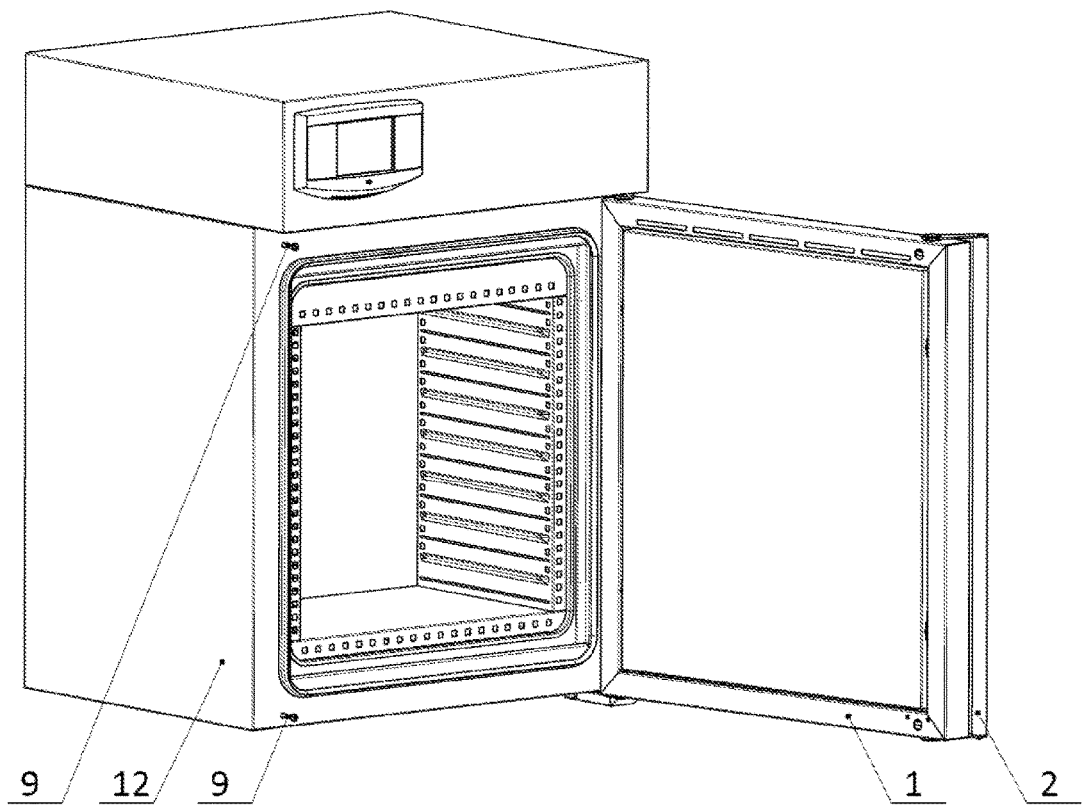
FIG. 5 shows the placement of the respective components of the door closing and securing mechanism on a cabinet and in a corresponding door.

The function of the closing and securing mechanism according to the present embodiment is as follows. In FIG. 1, the closing and securing mechanism is shown in its open position, the hook 8 resting on the coaxial end stop 7. The movements of the handle 2 and the hook 8 are rotational and the swinging end of the hook 8 moves along a curved trajectory. Turning the plate 3 in the direction of the arrow 13 (see FIG. 2) causes the hook 8 to move towards the fixed part 9 mounted on the cabinet 12 and to rest against the fixed part 9, as illustrated in FIG. 2. Then, the continuing rotational movement of the plate 3 causes the hook 8, which engages with the protrusion of the fixed part 9, to start pulling the door 1 towards the cabinet 12. If the door assumes its closed position, no moment of force will act on the plate 3. This means that the position of the plate 3 corresponding to the closed position of the door is maintained (see FIG. 3) by means of the friction produced by the center pin 10 or by means of the action of the tensile spring 11, as seen in FIG. 3. The tensile spring 11 is attached at its one end to the opening of the plate 3 in the vicinity of the center pin 10 and at its other end to the door 1, in order to secure the attachment of the plate 3 to the door 1.

INDUSTRIAL APPLICABILITY

The door closing and securing mechanism is suitable for operating doors of laboratory, medical and/or sterilization cabinets.

LIST OF REFERENCE NUMERALS

1 door
2 handle
3 plate
4.1 first flexible end stop
4.2 second flexible end stop
5 pivot
6 compression spring
7 coaxial end stop
8 hook
9 fixed part
10 center pin
11 tension spring
12 cabinet
13 arrow
14 movable part

The invention claimed is:

1. A closing and securing mechanism adapted for closing and securing doors of laboratory, medical, and sterilization cabinets, said closing and securing mechanism consisting of:
   a fixed part (9) attached to a cabinet (12), and a movable part (14) arranged in a door (1) of the cabinet;
   wherein the movable part (14) comprises a plate (3) provided with a first flexible end stop (4.1) and a second flexible end stop (4.2) in order to delimit the movement of the plate relative to the door (3);
   wherein the plate (3) is fixedly coupled with a handle (2) by a center pin (10), said center pin (10) forming a rotational axis of the handle (2), such that the handle is pivotally interconnected with the door (1), and the plate (3) having a coaxial end stop (7) concentric with the center pin (10) attached thereto, the coaxial end stop (7) providing support for a hook (8) associated with the plate;
   wherein the plate (3) is further provided with a pivot (5) eccentrically mounted with respect to the center pin (10), said pivot (5) forming a rotational axis for the hook (8), in which the hook is pivotally arranged with respect to the plate (3);
   wherein the hook (8) has a recess in a swinging end of the hook (8) that is distal from the pivot (5) for engaging a protrusion of the fixed part (9);
   wherein the rotational axis of the handle (2) is offset from the rotational axis of the hook (8); and
   wherein a tensile spring (11) is attached at its one end to the plate (3) and at its other end to the door (1) in order to secure the attachment of the plate (3) to the door (1), wherein a compression spring (6) is attached at its one end to the hook (8) and at its other end to the plate (3) in order to secure the attachment of the hook (8) to the fixed part (9).

2. The closing and securing mechanism of claim 1, wherein the tensile spring (11) is attached at its one end to the plate (3) in the vicinity of the center pin (10) and at its other end to the door (1), and wherein the compression spring (6) is attached at its one end to the hook (8) in the vicinity of the recess thereof and at its other end to the plate (3) in the vicinity of the second flexible end stop (4.2).

\* \* \* \* \*